United States Patent
Palushi et al.

(10) Patent No.: US 12,207,858 B2
(45) Date of Patent: Jan. 28, 2025

(54) APPARATUS AND METHOD FOR ABLATING EUSTACHIAN TUBE

(71) Applicants: Acclarent, Inc., Irvine, CA (US); Biosense Webster (Israel) Ltd., Yokneam (IL)

(72) Inventors: Jetmir Palushi, Irvine, CA (US); Hany Abdelwahed, Irvine, CA (US); Shubhayu Basu, Anaheim, CA (US); Itzhak Fang, Irvine, CA (US); Madison K. Vanosdoll, Irvine, CA (US); Henry F. Salazar, Pico Rivera, CA (US)

(73) Assignees: Acclarent, Inc., Irvine, CA (US); Biosense Webster (Israel) Ltd., Yokneam (IL)

(*) Notice: Subject to any disclaimer, the term of this patent is extended or adjusted under 35 U.S.C. 154(b) by 204 days.

(21) Appl. No.: 17/345,031

(22) Filed: Jun. 11, 2021

(65) Prior Publication Data
US 2021/0401479 A1    Dec. 30, 2021

Related U.S. Application Data

(60) Provisional application No. 63/043,203, filed on Jun. 24, 2020.

(51) Int. Cl.
*A61B 18/00* (2006.01)
*A61B 18/04* (2006.01)
(Continued)

(52) U.S. Cl.
CPC ............ *A61B 18/04* (2013.01); *A61L 29/085* (2013.01); *A61L 29/14* (2013.01);
(Continued)

(58) Field of Classification Search
None
See application file for complete search history.

(56) References Cited

U.S. PATENT DOCUMENTS 5,151,100 A * 9/1992 Abele ............... A61B 18/08
                                                607/113
5,277,201 A * 1/1994 Stern ............... A61N 1/40
                                                606/41

(Continued)

FOREIGN PATENT DOCUMENTS

| WO | WO 1999/032041 A1 | 7/1999 |
| WO | WO 2011/005903 A2 | 1/2011 |
| WO | WO 2011/025830 A1 | 3/2011 |

OTHER PUBLICATIONS

International Search Report and Written Opinion dated Aug. 25, 2021, for International Application No. PCT/IB2021/055319, 19 pages.

(Continued)

*Primary Examiner* — Linda C Dvorak
*Assistant Examiner* — Nicholas S Borsch
(74) *Attorney, Agent, or Firm* — Barnes & Thornburg LLP

(57) ABSTRACT

An apparatus includes a shaft, a balloon, a tip member, and a heating feature. The tip member is distal to the balloon and has a larger outer diameter than the shaft. The heating feature is operable to ablate tissue of the Eustachian tube contacting the balloon in the expanded state. The heating feature may include an illuminating element and a photosensitive coating on the balloon. Alternatively, the heating feature may include a thermal heating element that heats the balloon inflation fluid and thereby heats the wall of the balloon. Another apparatus includes a shaft, a tip member, and an electrode assembly. The electrode assembly includes a plurality of electrodes positioned along the shaft near the (Continued)

distal end, proximal to the tip member. The electrodes are spaced apart from each other along a longitudinal axis and are operable to apply RF energy to tissue to thereby ablate the tissue.

15 Claims, 8 Drawing Sheets

(51) Int. Cl.
*A61B 18/18* (2006.01)
*A61L 29/08* (2006.01)
*A61L 29/14* (2006.01)
*A61B 18/14* (2006.01)

(52) U.S. Cl.
CPC ............... *A61B 2018/00107* (2013.01); *A61B 2018/0022* (2013.01); *A61B 2018/00327* (2013.01); *A61B 2018/00577* (2013.01); *A61B 2018/00791* (2013.01); *A61B 18/1492* (2013.01); *A61B 2018/1807* (2013.01)

(56) References Cited

U.S. PATENT DOCUMENTS

| | | | |
|---|---|---|---|
| 5,344,398 A * | 9/1994 | Hara | A61B 18/18 604/21 |
| 5,571,153 A * | 11/1996 | Wallsten | A61F 7/12 604/114 |
| 6,109,268 A | 8/2000 | Thapliyal et al. | |
| 6,361,531 B1 | 3/2002 | Hissong | |
| 6,526,318 B1 | 3/2003 | Ansarinia | |
| 8,936,594 B2 | 1/2015 | Wolf et al. | |
| 9,072,597 B2 | 7/2015 | Wolf et al. | |
| 9,241,834 B2 | 1/2016 | Chang et al. | |
| 9,415,194 B2 | 8/2016 | Wolf et al. | |
| 9,687,288 B2 | 6/2017 | Saadat | |
| 10,485,609 B2 | 11/2019 | Palushi et al. | |
| 10,561,370 B2 | 2/2020 | Salazar et al. | |
| 10,595,935 B2 | 3/2020 | Gliner et al. | |
| 10,874,839 B2 | 12/2020 | Matlock et al. | |
| 11,027,105 B2 | 6/2021 | Matlock et al. | |
| 2003/0139789 A1 | 7/2003 | Tvinnereim et al. | |
| 2004/0186469 A1 | 9/2004 | Woloszko et al. | |
| 2004/0204747 A1 | 10/2004 | Kemeny et al. | |
| 2004/0215180 A1* | 10/2004 | Starkebaum | B64F 1/305 606/41 |
| 2005/0203597 A1* | 9/2005 | Yamazaki | A61B 18/1492 600/374 |
| 2005/0240147 A1* | 10/2005 | Makower | A61B 18/042 623/1.11 |
| 2005/0283148 A1 | 12/2005 | Janssen et al. | |
| 2006/0004323 A1 | 1/2006 | Chang et al. | |
| 2006/0095066 A1* | 5/2006 | Chang | A61B 17/12136 606/199 |
| 2007/0073364 A1 | 3/2007 | Meissner et al. | |
| 2009/0149849 A1 | 6/2009 | Lin et al. | |
| 2010/0087798 A1 | 4/2010 | Adams et al. | |
| 2010/0274164 A1 | 10/2010 | Juto | |
| 2010/0274188 A1 | 10/2010 | Chang et al. | |
| 2011/0130708 A1 | 6/2011 | Perry et al. | |
| 2012/0259217 A1 | 10/2012 | Gerrans et al. | |
| 2013/0274715 A1* | 10/2013 | Chan | A61B 17/22 604/514 |
| 2014/0364725 A1 | 12/2014 | Makower | |
| 2014/0371736 A1* | 12/2014 | Levin | A61B 18/082 606/28 |
| 2016/0067465 A1 | 3/2016 | Gerrans et al. | |
| 2016/0287055 A1 | 10/2016 | Kesten et al. | |
| 2016/0331459 A1 | 11/2016 | Townley et al. | |
| 2017/0027724 A1 | 2/2017 | Hossainy et al. | |
| 2017/0065324 A1 | 3/2017 | Attaluri et al. | |
| 2017/0252089 A1* | 9/2017 | Hester | A61B 18/1485 |
| 2019/0274887 A1 | 9/2019 | Godwin | |
| 2021/0169549 A1 | 6/2021 | Palushi et al. | |

OTHER PUBLICATIONS

U.S. Appl. No. 63/028,609, entitled "Shaft Deflection Control Assembly for ENT Guide Instrument," filed May 22, 2020.

Fukutake, Tomoshige, et al. "Laser surgery for allergic rhinitis." *Archives of Otolaryngology—Head & Neck Surgery* 112.12 (1986): 1280-1282.

Gindros, George, et al. "Mucosal changes in chronic hypertrophic rhinitis after surgical turbinate reduction." *European archives of oto-rhino-laryngology* 266.9 (2009): 1409-1416.

Ho, Ki-Hong Kevin, et al. "Electromechanical reshaping of septal cartilage." *The Laryngoscope* 113.11 (2003): 1916-1921.

* cited by examiner

APPARATUS AND METHOD FOR ABLATING EUSTACHIAN TUBE

PRIORITY

This application claims priority to U.S. Provisional Pat. App. No. 63/043,203, entitled "Apparatus and Method for Ablating Eustachian Tube," filed Jun. 24, 2020, the disclosure of which is incorporated by reference herein, in its entirety.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus.

In the context of Eustachian tube dilation, a dilation catheter or other dilation instrument may be inserted into the Eustachian tube and then be inflated or otherwise expanded to thereby dilate the Eustachian tube. The dilated Eustachian tube may provide improved ventilation from the nasopharynx to the middle ear and further provide improved drainage from the middle ear to the nasopharynx. Methods and devices for dilating the Eustachian tube are disclosed in U.S. Pub. No. 2010/0274188, entitled "Method and System for Treating Target Tissue within the ET," published on Oct. 28, 2010, now abandoned, the disclosure of which is incorporated by reference herein in its entirety; and U.S. Pub. No. 2013/0274715, entitled "Method and System for Eustachian Tube Dilation," published on Oct. 17, 2013, now abandoned, the disclosure of which is incorporated by reference herein in its entirety. An example of such a system is the Aera® Eustachian Tube Balloon Dilation System by Acclarent, Inc. of Irvine, California.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, California. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

An example of an electromagnetic IGS systems that may be used in ENT and sinus surgery is the CARTO® 3 System by Biosense-Webster, Inc., of Irvine, California When applied to functional endoscopic sinus surgery (FESS), balloon sinuplasty, and/or other ENT procedures, the use of IGS systems allows the surgeon to achieve more precise movement and positioning of the surgical instruments than can be achieved by viewing through an endoscope alone. As a result, IGS systems may be particularly useful during performance of FESS, balloon sinuplasty, and/or other ENT procedures where anatomical landmarks are not present or are difficult to visualize endoscopically.

It may be desirable to ablate tissue within a Eustachian tube, as part of a Eustachian tube dilation procedure or otherwise. While several systems and methods have been made and used to treat a Eustachian tube, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1A:
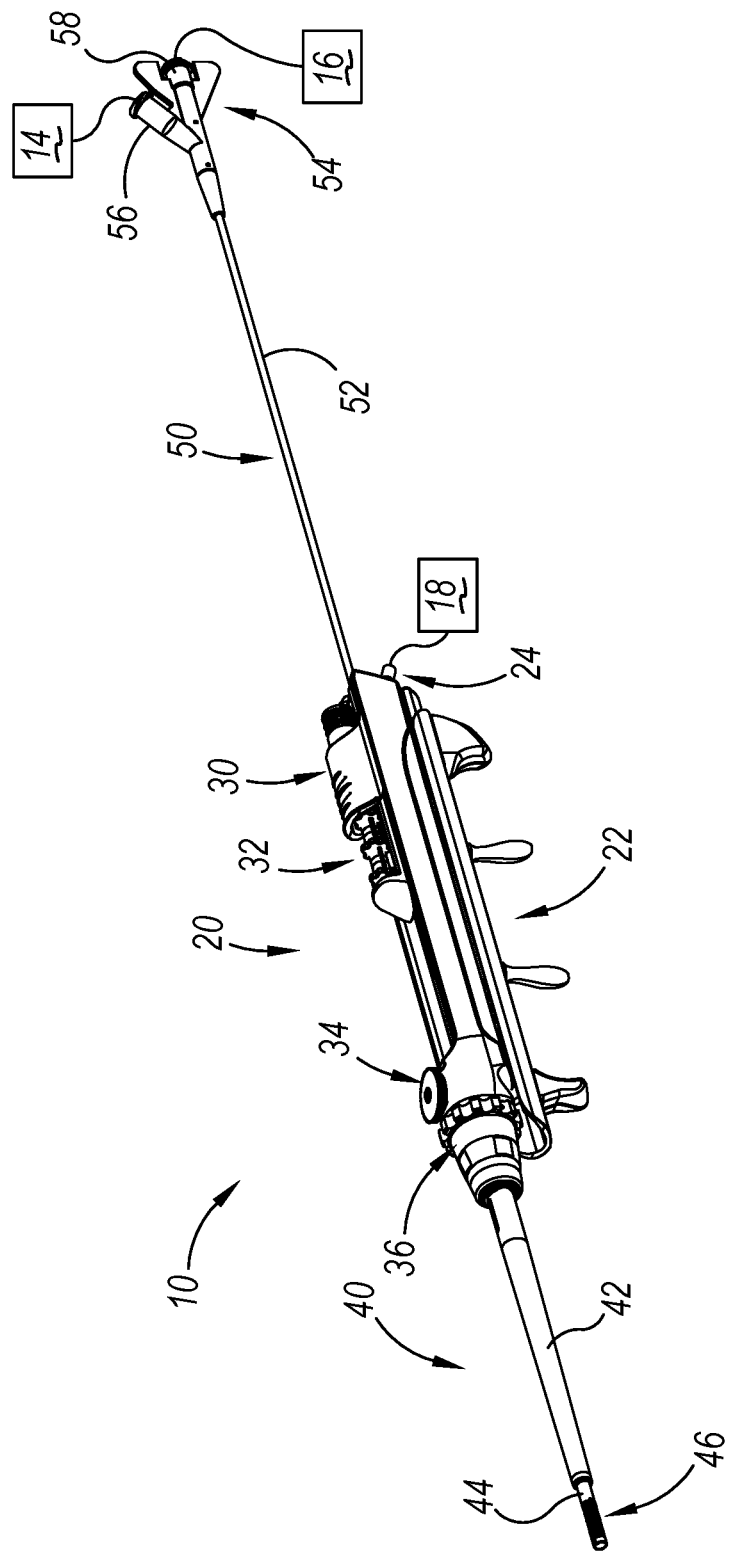
FIG. 1A depicts a perspective view of an example of a dilation instrument, with a dilation catheter in a proximal position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Example of Dilation Instrument

Figure 1B:
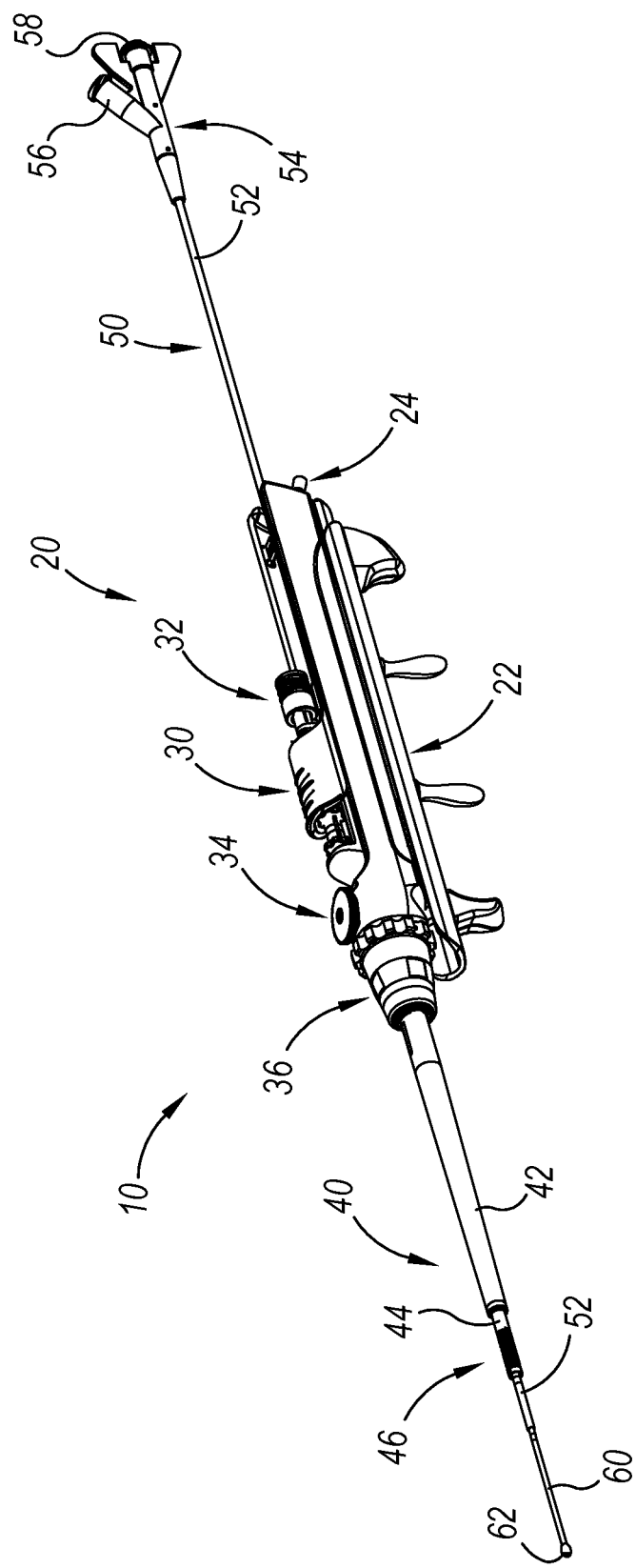
FIG. 1B depicts a perspective view of the instrument of FIG. 1A, with the dilation catheter in a distal position, and with a balloon of the dilation catheter in a non-expanded state.
Figure 1C:
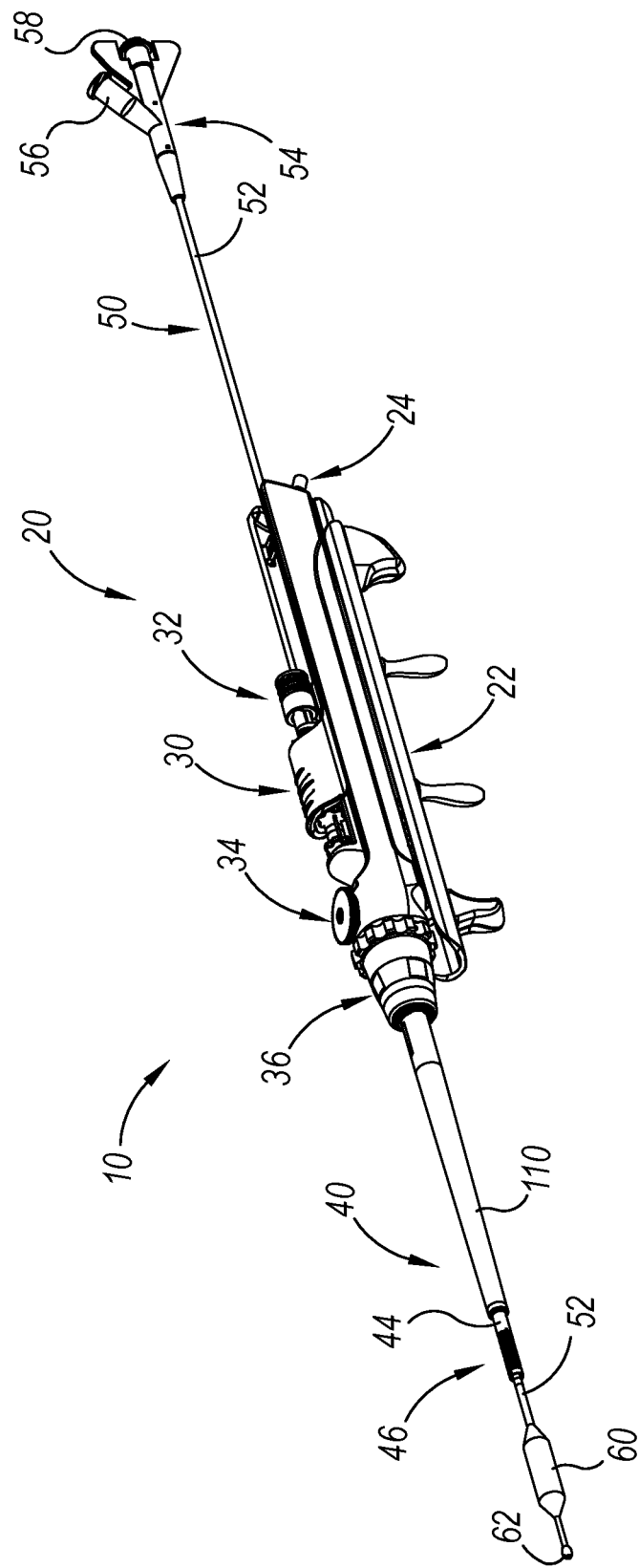
FIG. 1C depicts a perspective view of the instrument of FIG. 1A, with the dilation catheter in the distal position, and with the balloon of the dilation catheter in an expanded state.

FIGS. 1A-1C show an example of a dilation instrument (10) that may be used to dilate a Eustachian tube. While the discussion herein is provided mainly in the context of dilating a Eustachian tube, dilation instrument (10) may instead be used to dilate various other anatomical passageways within a patient, including but not limited to the ostium of a paranasal sinus, another passageway associated with drainage of a paranasal sinus, or some other anatomical passageway (e.g., within the ear, nose, or throat, etc.). As will be described in greater detail below, dilation instrument (10) of the present example provides adjustability that enables the operator to use dilation instrument (10) in different scenarios, without requiring the operator to switch between different instruments. For instance, dilation instrument (10) may be used to dilate various different anatomical passageways (e.g., frontal sinus ostium, frontal recess, maxillary sinus ostium, sphenoid sinus ostium, ethmoid sinus ostium, Eustachian tube, etc.) by making simple adjustments to structural features of the instrument.

Dilation instrument (10) of this example includes a handle assembly (20), a guide shaft assembly (40) extending distally from handle assembly (20); a guidewire actuation assembly (32) slidably coupled with handle assembly (20); a dilation catheter actuation assembly (30) slidably coupled with handle assembly (20); and a dilation catheter (50) slidably disposed in guide shaft assembly (40). In the present example, dilation catheter (50) is coaxially disposed within guide shaft assembly (40). In some other versions, guide shaft assembly (40) is coaxially disposed within dilation catheter (50). While a guidewire is omitted in the present example, other versions may include a guidewire that is coupled with guidewire actuation assembly (32), which may be operable to translate the guidewire longitudinally relative to guide shaft assembly (40) and rotate the guidewire about the longitudinal axis of the guidewire.

Dilation catheter (50) of this example includes a shaft (52), a connector (54), a balloon (60), and a distal tip (62). Balloon (60) of the present example is formed of a non-extensible material, though balloon (60) is still operable to transition between an expanded state (FIG. 1C) and a non-expanded state (FIG. 1B). In some other versions, balloon (60) is formed of an extensible material. Balloon (60) is in fluid communication with a lumen (not shown) formed through shaft (52). An inflation fluid source (14) and an irrigation fluid source (16) are coupled with connector (54) of dilation catheter (50). Connector is also in fluid communication with the lumen in shaft (52). In some versions, inflation fluid source (14) includes saline to inflate balloon (60) via the lumen formed through shaft (52), though any other suitable fluid may be used. Moreover, while balloon (60) is used as an expandable member to provide dilation of an anatomical passageway, any other suitable kind of dilator may be used. Dilation catheter actuation assembly (30) is secured to shaft (52) of dilation catheter (50), such that dilation catheter actuation assembly (30) is operable to translate dilation catheter (50) longitudinally relative to guide shaft assembly (40) as dilation catheter actuation assembly (30) is translated along handle assembly (20). Distal tip (62) of the present example is atraumatic (e.g., bulbous, blueberry-shaped, etc.) and is slightly larger than the diameter of shaft (52), such that distal tip (62) is configured to prevent dilation catheter (50) from passing through an isthmus (I) of a Eustachian tube (ET) as described in greater detail below. In some other versions, distal tip (62) is not enlarged relative to shaft (52); or has some other configuration.

A suction source (18) is coupled with guide shaft assembly (40) of dilation instrument (10) via a suction port (24) and a conduit (not shown) that spans through handle assembly (20). In some versions, suction source (18) and suction port (24) are omitted. In versions where suction source (18) and suction port (24) are included, suction may be applied within a patient via the open distal end of guide shaft assembly (40). Alternatively, suction may be applied via a cannula or other structure that is disposed on or in guide shaft assembly (40).

Handle assembly (20) includes a grip portion (22) and is sized and configured to be grasped and operated by a single hand of an operator. The operator may selectively operate guidewire actuation assembly (32) and dilation catheter actuation assembly (30) with the same single hand that grasps handle assembly (20). As shown in the transition from FIG. 1A to FIG. 1B, the operator may advance dilation catheter actuation assembly (30) distally along handle assembly (20) to thereby advance dilation catheter (50) distally, such that distal tip (62) of dilation catheter (50) is positioned distal to the distal end of guide shaft assembly (40). With dilation catheter (50) advanced to a distal position, the operator may then inflate a balloon (60) of dilation catheter (50) to achieve an expanded state as shown in FIG. 1C, to thereby dilate an anatomical passageway in which balloon (60) is positioned.

Guide shaft assembly (40) of the present example includes a rigid proximal portion (42) and a distal portion (44) having a flex section (44). Guide shaft assembly (40) is coupled with a first actuator (34) that is operable to drive flex section (44) to deflect toward and away from the longitudinal axis defined by proximal portion (42). First actuator (34) is supported by handle assembly (20) and is rotatable about an axis that is transverse to the longitudinal axis of proximal portion (42) to thereby drive deflection of flex section (44). By way of example only, guide shaft assembly (40) may include one or more pull wires or other components coupling flex section (44) with first actuator (34). Guide shaft assembly (40) is further coupled with a second actuator (36). Second actuator (36) is supported by handle assembly (20) and is rotatable about the longitudinal axis of proximal portion (42) to thereby rotate the entire guide shaft assembly (40) about the longitudinal axis of proximal portion (42), regardless of whether flex section (44) is in a straight or bent configuration. While first actuator (34) drives deflection of flex section (44) away from and toward the longitudinal axis of proximal portion (42), and second actuator (36) drives rotation of guide shaft assembly longitudinal axis of proximal portion (42), other configurations may be used. For instance, in some other versions, second actuator (36) drives deflection of flex section (44) away from and toward the longitudinal axis of proximal portion (42); and first actuator (34) drives rotation of guide shaft assembly longitudinal axis of proximal portion (42).

By way of further example only, control of guide shaft assembly (40), and/or any other aspects of instrument (10), may be provided in accordance with at least some of the teachings of U.S. Patent App. No. 63/028,609, entitled "Shaft Deflection Control Assembly for ENT Guide Instrument," filed May 22, 2020, the disclosure of which is incorporated by reference herein in its entirety; U.S. Pat. No. 10,874,839, entitled "Adjustable Instrument for Dilation of Anatomical Passageway," issued Dec. 29, 2020, the disclosure of which is incorporated by reference herein in its entirety; and/or U.S. Pat. No. 11,027,105, entitled "Adjustable Instrument for Dilation of Anatomical Passageway," issued Jun. 8, 2021, the disclosure of which is incorporated by reference herein in its entirety. Other variations of the features and functionalities described herein will be apparent to those skilled in the art in view of the teachings herein.

While not shown in FIGS. 1A-1C, one or more components of instrument (10) may include a position sensor that is operable to generate signals indicating where the position sensor is located within three-dimensional space. Such a position sensor may cooperate with field generating elements that generate an alternating electromagnetic field around a patient. Such a position sensor may be integrated into the distal end of guide shaft assembly (40), into distal tip (62) or some other component of dilation catheter (50), within a guidewire (not shown) that is secured to guidewire actuation assembly (32), and/or elsewhere within instrument (10). Such a position sensor may be configured to cooperate with a commercially available IGS system such as the CARTO® 3 System by Biosense-Webster, Inc., of Irvine, California Instrument (10) may thus be configured an operable in accordance with at least some of the teachings of U.S. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein in its entirety; and/or U.S. Pat. No. 10,561,370, entitled "Apparatus to Secure Field Generating Device to Chair," issued Feb. 18, 2020, the disclosure of which is incorporated by reference herein in its entirety. Alternatively, position sensing capabilities may be omitted.

II. Example of Eustachian Tube Dilation

Figure 2A:
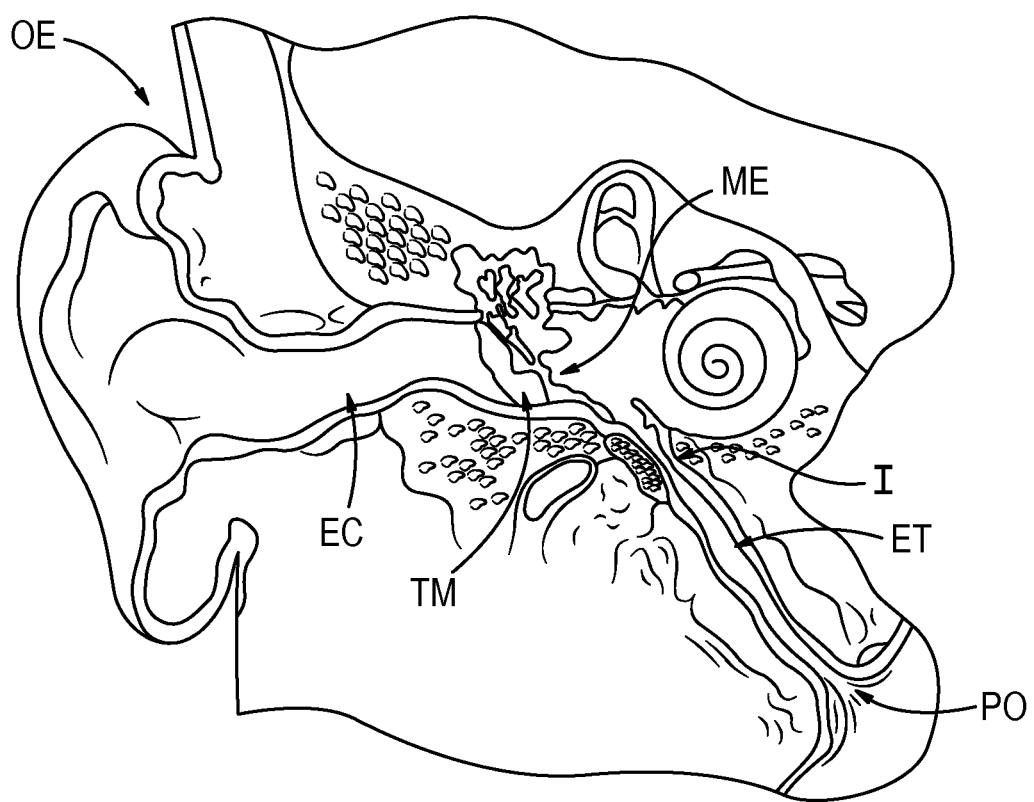
FIG. 2A depicts a cross-sectional view of a human ear showing the inner, middle and outer ear portions and the Eustachian tube connecting the middle ear with the nasopharynx region of the throat.

FIG. 2A shows anatomical structures associated with a patient's ear, including the outer ear (OE), the ear canal (EC), the tympanic membrane (TM), the middle ear (ME), and the Eustachian tube (ET). The Eustachian tube (ET) is in fluid communication with the nasopharynx via the pharyngeal ostium (PO). The isthmus (I) is a narrowed region (e.g., approximately 1 mm in diameter) between the Eustachian tube (ET) and the middle ear (ME). The Eustachian tube (ET) provides a pathway for ventilation from the nasopharynx to the middle ear (ME); and for drainage from the middle ear (ME) to the nasopharynx. When functioning properly, the Eustachian tube (ET) may open for a fraction of a second periodically in response to swallowing or yawning. In so doing, it allows air into the middle ear (ME) to replace air that has been absorbed by the middle ear lining (mucous membrane) or to equalize pressure changes occurring on altitude changes. In instances where fluid is built up in the middle ear (ME), an opened Eustachian tube (ET) also provides a pathway for such fluid to drain from the middle ear (ME) into the nasopharynx.

Figure 2B:
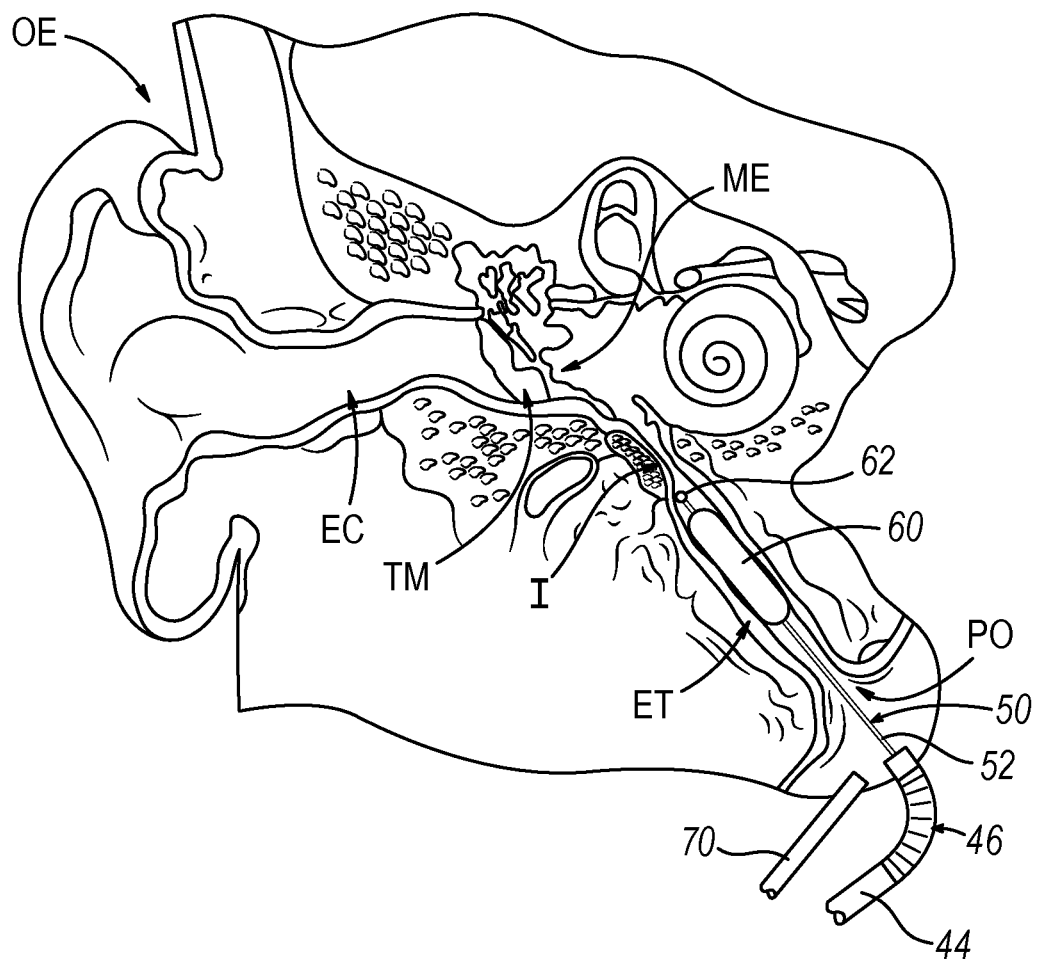
FIG. 2B depicts a cross-sectional view of the human ear of FIG. 2A, with the dilation catheter of the dilation instrument of FIG. 1A inserted in the Eustachian tube, and the balloon expanded to dilate the Eustachian tube.

In scenarios where the Eustachian tube (ET) remains persistently blocked or fails to open when it should, it may be desirable to dilate the Eustachian tube (ET). As shown in FIG. 2B, this may be carried out using dilation instrument (10) by inserting guide shaft assembly (40) through a patient's nose or mouth and positioning guide shaft assembly (40) in the nasopharynx such that the distal end of guide shaft assembly (40) is oriented toward the pharyngeal ostium (PO). This may be performed under visualization from an endoscope (70), if desired. As shown, first actuator (34) may be actuated to deflect flex section (46) toward the pharyngeal ostium (PO), thereby facilitating access to the pharyngeal ostium (PO). Dilation catheter actuation assembly (30) may be actuated to advance dilation catheter (50) distally relative to guide shaft assembly (40) to thereby position balloon (60) within the Eustachian tube (ET), and the balloon (60) may then be inflated to thereby dilate the Eustachian tube (ET) as shown in FIG. 2B.

When dilation catheter (50) is advanced distally relative to guide shaft assembly (40) to position balloon (60) within the Eustachian tube (ET), it may be warranted to take great care to avoid traversing the isthmus (I) with dilation catheter (50). This may ensure that instrumentation does not enter the middle ear (ME) and thereby damage the sensitive anatomical structures within the middle ear (ME). To that end, the enlarged distal tip (62) of dilation catheter (50) may engage the isthmus (I) and thereby arrest further distal advancement of dilation catheter (50) in the event that the operator tries to advance dilation catheter (50) too far.

In some instances, the operator may repeatedly inflate and deflate balloon (60) within the Eustachian tube (ET). Suitable numbers of inflation/deflation cycles of balloon (60) within the Eustachian tube (ET) will be apparent to those skilled in the art in view of the teachings herein. Similarly, suitable durations for maintaining balloon (60) in the inflated state within the Eustachian tube (ET) will be apparent to those skilled in the art in view of the teachings herein. In any case, once the operator is satisfied that the Eustachian tube (ET) has been sufficiently dilated, the operator may fully deflate balloon (60) and actuate dilation catheter actuation assembly (30) to retract dilation catheter (50) proximally relative to guide shaft assembly (40), thereby removing dilation catheter (50) from the Eustachian tube (ET). Instrument (10) may then be removed from the patient.

III. Examples of Eustachian Tube Ablation

In some patients, it may be desirable to ablate tissue within a Eustachian tube (ET). This may be desirable in some cases where the patient's Eustachian tube (ET) persistently remains in a patulous state, such that the Eustachian tube (ET) does not sufficiently close. A persistently patulous Eustachian tube (ET) may provide substantial discomfort to a patient. In some instances, substantial dilation of the Eustachian tube (ET) may cause cells of the Eustachian tube (ET) to regenerate, which may eventually lead to the Eustachian tube (ET) achieving a normally functioning, non-patulous state. In addition, or in the alternative, ablating the tissue of the Eustachian tube (ET) may provide a suitable treatment for a persistently patulous Eustachian tube (ET). For instance, such ablation may result in generation of scar tissue within the Eustachian tube (ET), which may eventually lead to the Eustachian tube (ET) achieving a normally functioning, non-patulous state. Alternatively, ablation may otherwise cause new cell generation within the Eustachian tube (ET), which may eventually lead to the Eustachian tube (ET) achieving a normally functioning, non-patulous state.

The following description provides examples of catheters (100, 200, 300, 400) that may be used to treat a persistently patulous Eustachian tube (ET) by at least ablating the tissue of the Eustachian tube (ET). In the case of catheters (100, 200), the treatment may also include dilating the Eustachian tube (ET). Any of the catheters (100, 200, 300, 400) described below may be used as part of instrument (10) described above, with a selected catheter (100, 200, 300, 400) replacing dilation catheter (50). Alternatively, any other suitable kind of instrumentation may be used to assist in inserting the working end of any of the below described catheters (100, 200, 300, 400) into the Eustachian tube (ET).

A. Example of Eustachian Tube Photodynamic Ablation

Figure 3A:
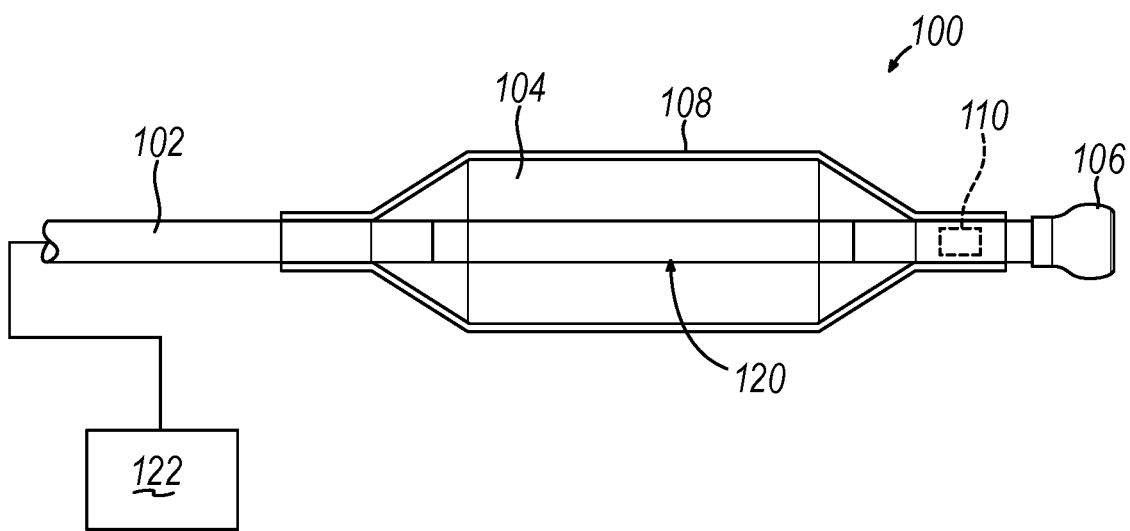
FIG. 3A depicts a side elevation view of a distal portion of an example of an alternative catheter that may be used to treat a Eustachian tube, with a balloon of the catheter in an expanded state, and with an illuminating element of the catheter in a non-activated state.
Figure 3B:
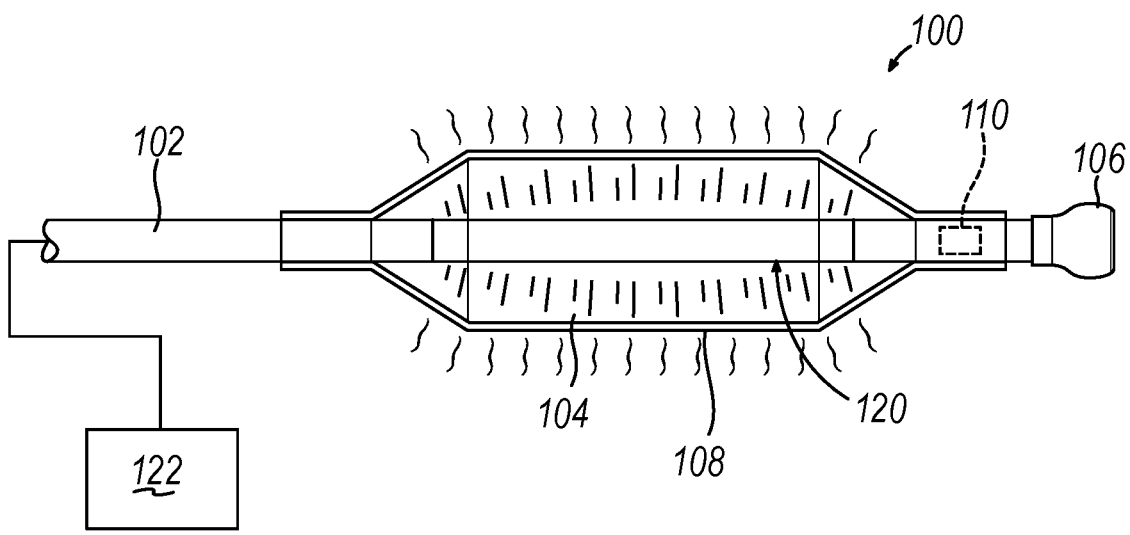
FIG. 3B depicts a side elevation view of the distal portion of the catheter of FIG. 3A, with the balloon of the catheter in the expanded state, and with the illuminating element of the catheter in an activated state.

FIGS. 3A-3B show a first example of a catheter (100) that may be used to treat a persistently patulous Eustachian tube (ET). As noted above, catheter (100) may be used as part of instrument (10) in place of dilation catheter (50). Catheter (100) of this example includes a shaft (102), a balloon (104), and a distal tip (106). Shaft (102) of the present example may be configured and operable substantially similar to shaft (52) of dilation catheter (50), except as otherwise described below. Shaft (102) may be flexible along its entire length, up to distal tip (106). Like balloon (60), balloon (104) of the present example may be configured to transition between a non-expanded state and an expanded state (though only the expanded state is shown in FIGS. 3A-3B). Balloon (104) may be formed of an extensible material or a non-extensible material. Distal tip (106) of the present example may be configured and operable substantially similar to distal tip (62) of dilation catheter (50). Distal tip (106) may thus prevent catheter (100) from being advanced through the isthmus (I) between the Eustachian tube (ET) and the middle ear (ME).

Shaft (102) of catheter (100) is unlike shaft (52) of catheter (50) in that shaft (102) includes an integral illuminating element (120). Illuminating element (120) is positioned within the interior of balloon (104) and is operable to emit light through the fluid inflating balloon (104). By way of example only, illuminating element (120) may include one or more LEDs or other electrically activated sources of light integrated in shaft (102). A power source (122) that is coupled with illuminating element (120) may include an electrical power source that is operable to drive such LEDs or other electrically activated sources of light forming illuminating element (120). In such versions, wires may extend along the length of shaft (102) to couple illuminating element (120) with power source (122). In some other versions, illuminating element (120) may include one or more optically transmissive windows, and power source (122) may include a source of light. In such versions, power source (122) may be coupled with illuminating element (120) via one or more optical fibers, light pipes, or other structures that are operable to convey light. Other suitable components that may be used to form illuminating element (120) and power source (122) will be apparent to those skilled in the art in view of the teachings herein.

Balloon (104) of catheter (100) is unlike balloon (60) of catheter (50) in that balloon (104) includes a coating (108) along the exterior of balloon (104). In the present example, coating (108) is configured to achieve photodynamic therapy of tissue contacting coating (108). Photodynamic therapy may employ non-toxic dyes known as photosensitizers, which may absorb visible light to produce an excited singlet state, followed by a triplet state that may undergo photochemistry. In the presence of ambient oxygen, reactive oxygen species, such as singlet oxygen and hydroxyl radicals may be formed that are capable of ablating tissue cells. Thus, when coating (108) receives light from illuminating element (120), coating (108) releases oxygen that is capable of ablating tissue that is in contact with balloon (104). By way of example only, the photosensitizer of coating (108) may include hemoglobin. Alternatively, any other suitable photosensitizer may be used. Various suitable formulations that may be used to form coating (108) will be apparent to those skilled in the art in view of the teachings herein.

In use, catheter (100) may be introduced into the Eustachian tube (ET) via shaft assembly (40), using the procedure shown in FIGS. 2B-2B and describe above. Balloon (104) may be in a non-expanded state during the act of positioning. Once catheter (100) is advanced to a point where balloon (104) is suitably positioned in the Eustachian tube (ET), inflation fluid source (14) may be activated to transition balloon (104) to the expanded state, as shown in FIG. 3A. In some scenarios, having balloon (104) in the expanded state within the Eustachian tube (ET) will cause dilation of the Eustachian tube (ET). In some other scenarios, having balloon (104) in the expanded state within the Eustachian tube (ET) will simply cause coating (108) to bear against tissue of the Eustachian tube (ET), without necessarily also causing dilation of the Eustachian tube (ET). In either case, coating (108) may contact the tissue of the Eustachian tube (ET) along all or at least a portion of the length of balloon (104) when balloon (104) is expanded within the Eustachian tube (ET).

While balloon (104) is expanded within the Eustachian tube (ET), power source (122) may be activated to provide illumination via illuminating element (120). Light emitted from illuminating element (120) may pass through the fluid inflating balloon (120) and reach coating (108). In response to the illumination from illuminating element (120), coating (108) may heat up as shown in FIG. 3B and ablate the tissue of the Eustachian tube (ET) contacting coating (108). This photodynamic ablation of the tissue of the Eustachian tube (ET) may ultimately generate scar tissue in the Eustachian tube (ET). This generated scar tissue in the Eustachian tube (ET) (and, in some cases, combined with tissue effects caused by dilation from balloon (104)) may ultimately result in narrowing of the passageway through the Eustachian tube (ET), which may in turn alleviate an otherwise persistently patulous Eustachian tube (ET). Catheter (100) may thus be used to treat a persistently patulous Eustachian tube (ET) by providing ablation via photodynamic therapy.

In some versions of catheter (100) at least one position sensor (110) is integrated into catheter (100). Such a position sensor (110) may be configured to cooperate with an IGS system and thereby provide data indicating the position of catheter (100) within three-dimensional space as described above. As shown in FIGS. 3A-3B, such a position sensor (110) may be located in shaft (102) between balloon (104) and distal tip (106). In addition, or in the alternative, such a position sensor (110) may be located in distal tip (106). In addition, or in the alternative, such a position sensor (110) may be located elsewhere within shaft (102). Some versions of catheter (100) may simply omit position sensor (110) altogether.

B. Example of Eustachian Tube Thermal Ablation

Figure 4A:
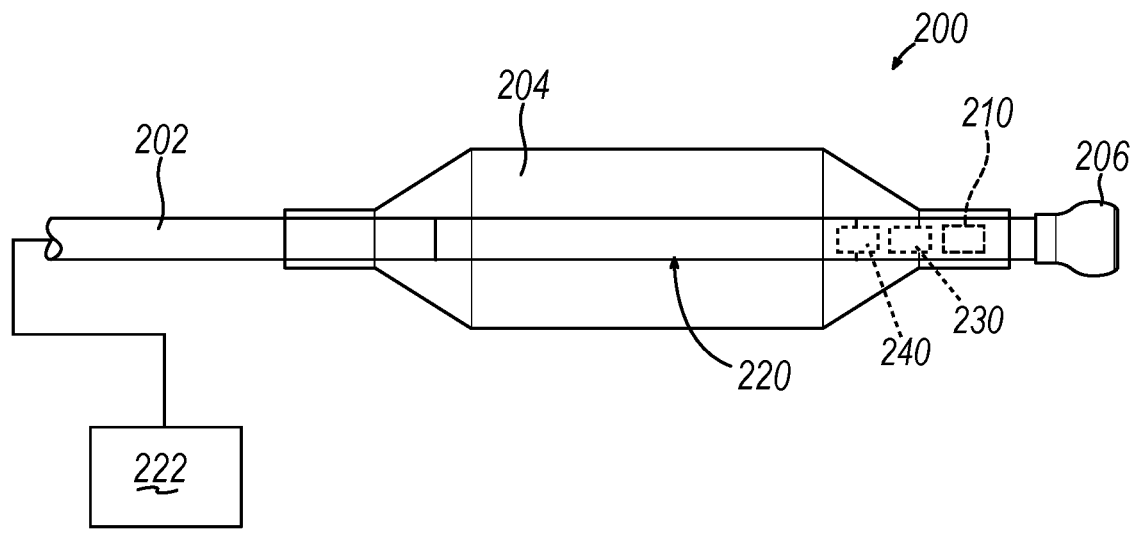
FIG. 4A depicts a side elevation view of a distal portion of an example of another alternative catheter that may be used to treat a Eustachian tube, with a balloon of the catheter in an expanded state, and with a heating element of the catheter in a non-activated state.
Figure 4B:
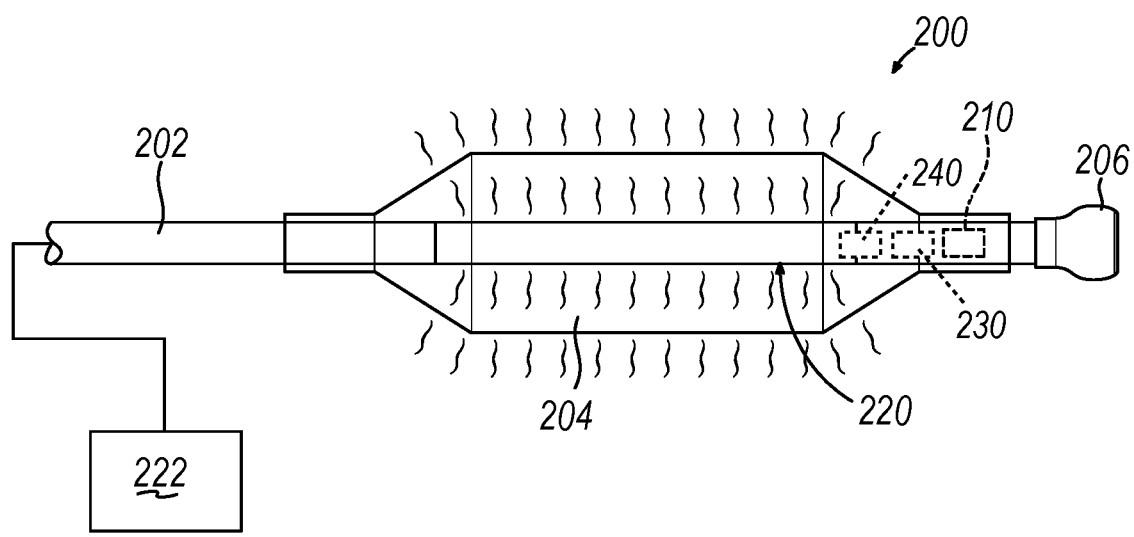
FIG. 4B depicts a side elevation view of the distal portion of the catheter of FIG. 4A, with the balloon of the catheter in the expanded state, and with the heating element of the catheter in an activated state.

FIGS. 4A-4B show a second example of a catheter (200) that may be used to treat a persistently patulous Eustachian tube (ET). As noted above, catheter (200) may be used as part of instrument (10) in place of dilation catheter (50). Catheter (200) of this example includes a shaft (202), a balloon (204), and a distal tip (206). Shaft (202) of the present example may be configured and operable substantially similar to shaft (52) of dilation catheter (50), except as otherwise described below. Shaft (202) may be flexible along its entire length, up to distal tip (206). Like balloon (60), balloon (204) of the present example may be configured to transition between a non-expanded state and an expanded state (though only the expanded state is shown in FIGS. 4A-4B). Balloon (204) may be formed of an extensible material or a non-extensible material. Distal tip (206) of the present example may be configured and operable substantially similar to distal tip (62) of dilation catheter (50). Distal tip (206) may thus prevent catheter (200) from being advanced through the isthmus (I) between the Eustachian tube (ET) and the middle ear (ME).

Shaft (202) of catheter (200) is unlike shaft (52) of catheter (50) in that shaft (202) includes an integral heating element (220). Heating element (220) is positioned within the interior of balloon (204) and is operable to thermally heat the fluid inflating balloon (204). By way of example only, heating element (220) may include one or more electrically resistive heating elements. A power source (222) that is coupled with heating element (220) may include an electrical power source that is operable to drive such electrically resistive heating elements other electrically activated sources of heat forming heating element (220). In such versions, wires may extend along the length of shaft (202) to couple heating element (220) with power source (222). Other suitable components that may be used to form heating element (220) and power source (222) will be apparent to those skilled in the art in view of the teachings herein.

In some versions, catheter (200) further includes a temperature sensor (230) that is in thermal communication with the fluid inflating balloon (204). Such a temperature sensor (230) may thus sense the temperature of the fluid inflating balloon (204). Temperature data from temperature sensor (230) may be used to regulate heating of the fluid by heating element (220) to ensure that a desired temperature is achieved; and to prevent the fluid from being overheated. By way of example only, temperature sensor (230) may include a thermocouple. Other suitable forms that temperature sensor (230) may take, as well as various ways in which temperature sensor (230) may be used, will be apparent to those skilled in the art in view of the teachings herein. In some other versions, temperature sensor (230) is omitted from catheter (200).

Also in some versions, catheter (200) further includes a recirculating feature (240) that is operable to circulate the inflation fluid within balloon (204). Such a recirculating feature (240) may thus facilitate even distribution of heat within the interior of balloon (204). Such a recirculating feature (240) may include an inlet and an outlet, with a pump or other feature that is used to drive fluid between the inlet and outlet. While recirculating feature (240) is shown schematically as being placed near the distal end of balloon (204), some versions may include one or more components of recirculating feature (240) at one or more other regions of shaft (202). For instance, an inlet of recirculating feature (240) may be positioned near the proximal end of balloon (204) while an outlet of recirculating feature (240) may be positioned near the distal end of balloon (204). Other suitable components and arrangements that may be used to provide recirculating feature (240) will be apparent to those skilled in the art in view of the teachings herein. In some other versions, recirculating feature (240) is omitted from catheter (200).

In use, catheter (300) may be introduced into the Eustachian tube (ET) via shaft assembly (40), using the procedure shown in FIGS. 2B-2B and describe above. Balloon (204) may be in a non-expanded state during the act of positioning. Once catheter (300) is advanced to a point where balloon (204) is suitably positioned in the Eustachian tube (ET), inflation fluid source (14) may be activated to transition balloon (204) to the expanded state, as shown in FIG. 4A. In some scenarios, having balloon (204) in the expanded state within the Eustachian tube (ET) will cause dilation of the Eustachian tube (ET). In some other scenarios, having balloon (204) in the expanded state within the Eustachian tube (ET) will simply cause balloon (204) to bear against tissue of the Eustachian tube (ET), without necessarily also causing dilation of the Eustachian tube (ET). In either case, balloon (204) may contact the tissue of the Eustachian tube (ET) along all or at least a portion of the length of balloon (204) when balloon (204) is expanded within the Eustachian tube (ET).

While balloon (204) is expanded within the Eustachian tube (ET), power source (222) may be activated to heat the inflation fluid via heating element (220). Heat from the heated inflation fluid may pass through the material forming balloon (204) as shown in FIG. 4B and thereby ablate the tissue of the Eustachian tube (ET) contacting balloon (204). By way of example only, the inflation fluid may be heated to approximately 95 degrees Celsius using heating element (220). Balloon (204) may be formed from silicone or any other suitable material, to the extent that such material may generally withstand temperatures above 100 degrees Celsius. Since cell ablation may begin above approximately 45 degrees Celsius, using heated inflation fluid at a temperature above that needed for cell ablation (yet below the melting point of balloon (204)) may result in ablation throughout the contacted tissue of the Eustachian tube (ET). This thermal ablation of the tissue of the Eustachian tube (ET) may ultimately generate scar tissue in the Eustachian tube (ET). This generated scar tissue in the Eustachian tube (ET) (and, in some cases, combined with tissue effects caused by dilation from balloon (204)) may ultimately result in narrowing of the passageway through the Eustachian tube (ET), which may in turn alleviate an otherwise persistently patulous Eustachian tube (ET). Catheter (200) may thus be used to treat a persistently patulous Eustachian tube (ET) by providing thermal ablation.

In some versions of catheter (200) at least one position sensor (210) is integrated into catheter (200). Such a position sensor (210) may be configured to cooperate with an IGS system and thereby provide data indicating the position of catheter (200) within three-dimensional space as described above. As shown in FIGS. 4A-4B, such a position sensor (210) may be located in shaft (202) between balloon (204) and distal tip (206). In addition, or in the alternative, such a position sensor (210) may be located in distal tip (206). In addition, or in the alternative, such a position sensor (210) may be located elsewhere within shaft (202). Some versions of catheter (200) may simply omit position sensor (210) altogether.

C. Example of Eustachian Tube RF Ablation

Figure 5:
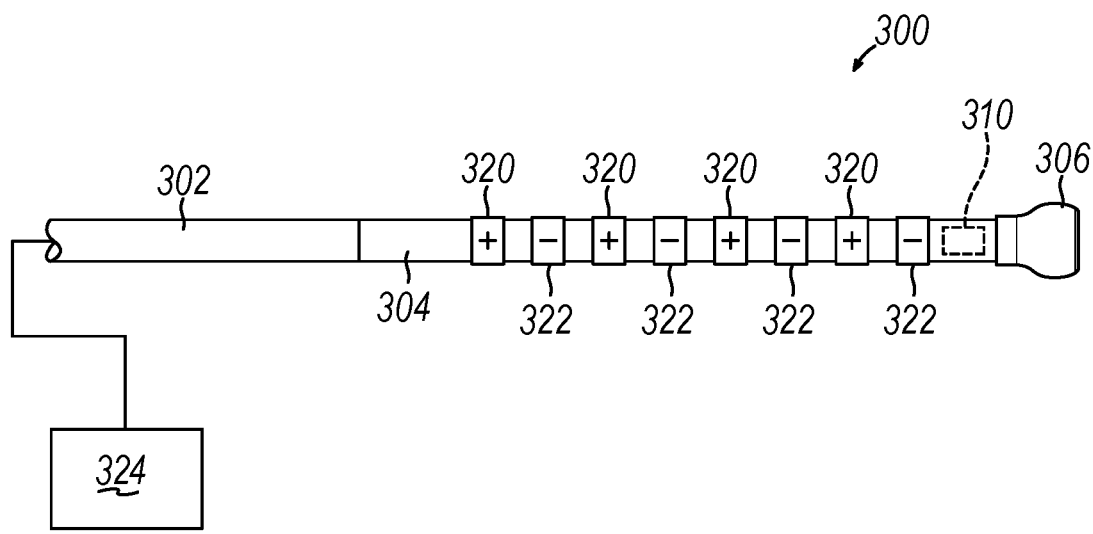
FIG. 5 depicts a side elevation view of a distal portion of an example of another alternative catheter that may be used to treat a Eustachian tube.
Figure 6:
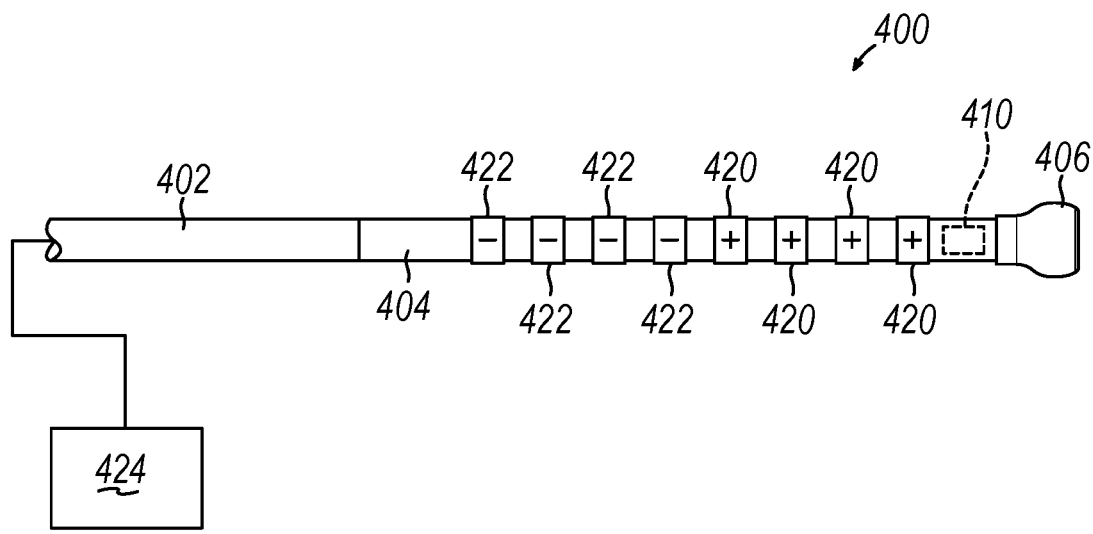
FIG. 6 depicts a side elevation view of a distal portion of an example of another alternative catheter that may be used to treat a Eustachian tube.

Another method of ablating tissue includes application of radiofrequency (RF) electrical energy to the tissue. Such RF ablation may be bipolar or monopolar. In bipolar RF ablation, at least two electrodes of opposing polarity of an instrument end effector are placed against the tissue and electrically activated. In monopolar ablation, an instrument end effector has one or more electrodes that are only of one (active) polarity, while a ground (return) pad is placed under the patient or adhered to the skin of the patient. In either case, the tissue contacting the electrode(s) of the instrument end effector may be ablated through application of RF energy at an appropriate amplitude. FIGS. 5 and 6 show examples of catheters (300, 400) with end effectors that are operable to apply bipolar ablation to tissue. As noted above, either catheter (300, 400) may be used as part of instrument (10) in place of dilation catheter (50).

As shown in FIG. 5, catheter (300) includes a flexible shaft (302), an electrode assembly (304), and a distal tip (306). Shaft (302) of the present example may be configured and operable substantially similar to shaft (52) of dilation catheter (50), except as otherwise described below. Shaft (302) may be flexible along its entire length, up to distal tip (306). In some versions, the flexibility of shaft (302) may vary along the length of shaft (302). For instance, the distal portion of shaft (302) including electrode assembly (304) may be more flexible than the portion of shaft (302) proximal to electrode assembly (304). Alternatively, the distal portion of shaft (302) including electrode assembly (304) may be less flexible than the portion of shaft (302) proximal to electrode assembly (304). Distal tip (306) of the present example may be configured and operable substantially similar to distal tip (62) of dilation catheter (50). Distal tip (306) may thus prevent catheter (300) from being advanced through the isthmus (I) between the Eustachian tube (ET) and the middle ear (ME).

Unlike catheters (50, 100, 200) described above, catheter (300) of this example lacks a balloon. Instead, electrode assembly (304) is located on the distal region of shaft (302), substantially where balloon (60, 104, 204) would be located on catheter (50, 100, 200). In some versions, electrode assembly (304) is longer than balloon (60, 104, 204), while in other versions electrode assembly (304) is shorter than or the same length as balloon (60, 104, 204). Electrode assembly (304) of the present example includes a plurality of electrodes (320, 322), which are in the form of annular rings that are longitudinally spaced apart from each other along the length of electrode assembly (304). While electrodes (320, 322) are annular in the present example, electrodes (320, 322) may instead take any other suitable form as will be apparent to those skilled in the art in view of the teachings herein. By way of further example only, electrode assembly (304) may include a spine (not shown) formed of a resilient material (e.g., nitinol, etc.), with an insulating sheath (not shown) positioned over the spine, and with electrodes (320, 322) positioned over the insulating sheath. Other suitable components and arrangements will be apparent to those skilled in the art in view of the teachings herein.

Electrodes (320, 322) of the present example are coupled with an electrical power source (324), which is operable to energize electrodes (320, 322). Electrodes (320, 322) may be coupled with power source (324) via wires extending along the length of shaft (302). Each electrode (320) is configured to serve as an active electrode, while each electrode (322) is configured to serve as a return electrode, such that electrodes (320, 322) cooperate to provide bipolar ablation of tissue contacting electrodes (320, 322). In the present example, the positioning of electrodes (320, 322) alternates along the length of electrode assembly (304). This arrangement may be particularly suitable for providing relatively shallow ablation, establishing ablation lesions that are relatively close to the surface of tissue contacting electrodes (320, 322).

In some versions, electrodes (320, 322) are also used to sense impedance of tissue contacting electrodes (320, 322) during the ablation procedure. Such impedance may represent the state of the tissue (e.g., indicating whether the ablation is complete, etc.). Such impedance may thus be used to regulate delivery of power from power source (324). In addition, or in the alternative, other kinds of sensors (e.g., a temperature sensor) may be integrated into catheter (300) to provide real-time feedback indicating the state of tissue contacting electrodes (320, 322) during the ablation procedure. Other suitable ways in which the real-time state of tissue contacting electrodes (320, 322) may be monitored during an ablation procedure, and ways in which such information may be utilized to regulate delivery of RF energy to the tissue, will be apparent to those skilled in the art in view of the teachings herein.

In use, catheter (300) may be introduced into the Eustachian tube (ET) via shaft assembly (40), using the procedure shown in FIGS. 2B-2B and describe above. Once catheter (300) is advanced to a point where electrode assembly (304) is suitably positioned in the Eustachian tube (ET), power source (324) may be activated to apply bipolar RF energy via electrodes (320, 322) to tissue contacting electrodes (320, 322). This RF ablation of the tissue of the Eustachian tube (ET) may ultimately generate scar tissue in the Eustachian tube (ET). This generated scar tissue in the Eustachian tube (ET) (and, in some cases, combined with tissue effects caused by dilation from balloon (104)) may ultimately result in narrowing of the passageway through the Eustachian tube (ET), which may in turn alleviate an otherwise persistently patulous Eustachian tube (ET). Catheter (300) may thus be used to treat a persistently patulous Eustachian tube (ET) by providing RF ablation. In some cases, a dilation catheter like catheter (50) is used first, to dilate the Eustachian tube (ET), before catheter (300) is used to perform RF ablation of the Eustachian tube (ET).

In some versions of catheter (300) at least one position sensor (310) is integrated into catheter (300). Such a position sensor (310) may be configured to cooperate with an IGS system and thereby provide data indicating the position of catheter (300) within three-dimensional space as described above. As shown in FIG. 5, such a position sensor (310) may be located in shaft (302) between the distal-most electrode (322) and distal tip (306). In addition, or in the alternative, such a position sensor (310) may be located in distal tip (306). In addition, or in the alternative, such a position sensor (310) may be located elsewhere within shaft (302). Some versions of catheter (300) may simply omit position sensor (310) altogether.

Catheter (400) is substantially similar to catheter (300), except for the differences noted below. As shown in FIG. 4, catheter (400) includes a flexible shaft (402), an electrode assembly (404), and a distal tip (406). Shaft (402) of the present example may be configured and operable substantially similar to shaft (52) of dilation catheter (50), except as otherwise described below. Shaft (402) may be flexible along its entire length, up to distal tip (406). In some versions, the flexibility of shaft (402) may vary along the length of shaft (402). For instance, the distal portion of shaft (402) including electrode assembly (404) may be more flexible than the portion of shaft (402) proximal to electrode assembly (404). Alternatively, the distal portion of shaft (402) including electrode assembly (404) may be less flexible than the portion of shaft (402) proximal to electrode assembly (404). Distal tip (406) of the present example may be configured and operable substantially similar to distal tip (62) of dilation catheter (50). Distal tip (406) may thus prevent catheter (400) from being advanced through the isthmus (I) between the Eustachian tube (ET) and the middle ear (ME).

Unlike catheters (50, 100, 200) described above, catheter (400) of this example lacks a balloon. Instead, electrode assembly (404) is located on the distal region of shaft (402), substantially where balloon (60, 104, 204) would be located on catheter (50, 100, 200). In some versions, electrode assembly (404) is longer than balloon (60, 104, 204), while in other versions electrode assembly (404) is shorter than or the same length as balloon (60, 104, 204). Electrode assembly (404) of the present example includes a plurality of electrodes (420, 422), which are in the form of annular rings that are longitudinally spaced apart from each other along the length of electrode assembly (404). While electrodes (420, 422) are annular in the present example, electrodes (420, 422) may instead take any other suitable form as will be apparent to those skilled in the art in view of the teachings herein. By way of further example only, electrode assembly (404) may include a spine (not shown) formed of a resilient material (e.g., nitinol, etc.), with an insulating sheath (not shown) positioned over the spine, and with electrodes (420, 422) positioned over the insulating sheath. Other suitable components and arrangements will be apparent to those skilled in the art in view of the teachings herein.

Electrodes (420, 422) of the present example are coupled with an electrical power source (424), which is operable to energize electrodes (420, 422). Electrodes (420, 422) may be coupled with power source (424) via wires extending along the length of shaft (402). Each electrode (420) is configured to serve as an active electrode, while each electrode (422) is configured to serve as a return electrode, such that electrodes (420, 422) cooperate to provide bipolar ablation of tissue contacting electrodes (420, 422). In the present example, electrodes (420, 422) are positioned and arranged such that electrodes (420) are all grouped together along the distal portion of electrode assembly (404), while electrodes (423) are all grouped together along the proximal portion of electrode assembly (404). This arrangement may be particularly suitable for providing relatively deep ablation, establishing ablation lesions that are relatively far from the surface of tissue contacting electrodes (420, 422). In other words, catheter (300) may be particularly suited for relatively shallow ablation while catheter (400) may be particularly suited for relatively deep ablation.

In some versions, electrodes (420, 422) are also used to sense impedance of tissue contacting electrodes (420, 422) during the ablation procedure. Such impedance may represent the state of the tissue (e.g., indicating whether the ablation is complete, etc.). Such impedance may thus be used to regulate delivery of power from power source (424). In addition, or in the alternative, other kinds of sensors (e.g., a temperature sensor) may be integrated into catheter (400) to provide real-time feedback indicating the state of tissue contacting electrodes (420, 422) during the ablation procedure. Other suitable ways in which the real-time state of tissue contacting electrodes (420, 422) may be monitored during an ablation procedure, and ways in which such information may be utilized to regulate delivery of RF energy to the tissue, will be apparent to those skilled in the art in view of the teachings herein.

In use, catheter (400) may be introduced into the Eustachian tube (ET) via shaft assembly (40), using the procedure shown in FIGS. 2B-2B and describe above. Once catheter (400) is advanced to a point where electrode assembly (404) is suitably positioned in the Eustachian tube (ET), power source (424) may be activated to apply bipolar RF energy via electrodes (420, 422) to tissue contacting electrodes (420, 422). This RF ablation of the tissue of the Eustachian tube (ET) may ultimately generate scar tissue in the Eustachian tube (ET). This generated scar tissue in the Eustachian tube (ET) (and, in some cases, combined with tissue effects caused by dilation from balloon (104)) may ultimately result in narrowing of the passageway through the Eustachian tube (ET), which may in turn alleviate an otherwise persistently patulous Eustachian tube (ET). Catheter (400) may thus be used to treat a persistently patulous Eustachian tube (ET) by providing RF ablation. In some cases, a dilation catheter like catheter (50) is used first, to dilate the Eustachian tube (ET), before catheter (400) is used to perform RF ablation of the Eustachian tube (ET).

In some versions of catheter (400) at least one position sensor (410) is integrated into catheter (400). Such a position sensor (410) may be configured to cooperate with an IGS system and thereby provide data indicating the position of catheter (400) within three-dimensional space as described above. As shown in FIG. 6, such a position sensor (410) may be located in shaft (402) between the distal-most electrode (420) and distal tip (406). In addition, or in the alternative, such a position sensor (410) may be located in distal tip (406). In addition, or in the alternative, such a position sensor (410) may be located elsewhere within shaft (402). Some versions of catheter (400) may simply omit position sensor (410) altogether.

While the above-described versions of catheters (300, 400) are described as being operable to provide bipolar RF energy, either catheter (300, 400) may instead be configured to provide monopolar RF energy. In particular, electrodes (320, 322, 420, 422) may all be configured to provide only one (active) polarity, while a ground (return) pad is placed under the patient or adhered to the skin of the patient. Moreover, some versions of catheters (300, 400) may be operable to switch between providing bipolar RF energy and monopolar RF energy, based on a selection by an operator. Various ways in which either catheter (300, 400) may be used to provide monopolar RF energy, and various ways in which either catheter (300, 400) may be selectively switched between providing bipolar RF energy and monopolar RF energy, will be apparent to those skilled in the art in view of the teachings herein.

IV. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a shaft defining a lumen, the shaft having a first outer diameter; (b) a balloon at the distal end of the shaft, the balloon being in fluid communication with the lumen, the balloon being operable to transition between a non-expanded state and an expanded state, the balloon in the non-expanded state being sized to fit in a Eustachian tube of a patient, the balloon in the expanded state being sized to bear against tissue of the Eustachian tube; (c) a tip member at the distal end of the shaft, the tip member being positioned distal to the balloon, the tip member having a second outer diameter, the second outer diameter being larger than the first outer diameter; and (d) a heating feature, the heating feature being operable to ablate tissue of the Eustachian tube contacting the balloon in the expanded state.

Example 2

The apparatus of claim 1, the balloon being formed of a non-extensible material.

Example 3

The apparatus of any one or more of Examples 1 through 2, the tip member having a bulb shape.

Example 4

The apparatus of any one or more of Examples 1 through 3, the second outer diameter being sized to prevent the tip member from passing through an isthmus between a Eustachian tube and middle ear of a patient.

Example 5

The apparatus of any one or more of Examples 1 through 4, the heating feature including an illuminating element.

Example 6

The apparatus of claim 5, the illuminating element being positioned within an interior region of the balloon.

Example 7

The apparatus of any one or more of Examples 5 through 6, the illuminating element including an LED within an interior region of the balloon.

Example 8

The apparatus of claim 7, further comprising an electrical power source in communication with the LED, the electrical power source being operable to activate the LED.

Example 9

The apparatus of any one or more of Examples 5 through 8, the illuminating element including an optically transmissive window on the shaft.

Example 10

The apparatus of claim 9, further comprising a light source, the optically transmissive window being operable to emit light from the light source into the interior region of the balloon.

Example 11

The apparatus of claim 10, further comprising a light conveying feature extending along the shaft, the light conveying feature being configured to optically couple the light source with the optically transmissive window.

Example 12

The apparatus of claim 11, the light conveying feature being selected from the group consisting of a light pipe and an optical fiber.

Example 13

The apparatus of any one or more of Examples 5 through 12, the heating feature further including a light sensitive coating on the balloon, the light sensitive coating being configured to ablate tissue in response to light from the illuminating element.

Example 14

The apparatus of claim 13, the light sensitive coating comprising hemoglobin.

Example 15

The apparatus of any one or more of Examples 1 through 14, the heating feature including a thermal heating element.

Example 16

The apparatus of claim 15, the thermal heating element being positioned within an interior region of the balloon.

Example 17

The apparatus of any one or more of Examples 15 through 16, the thermal heating element including a resistive heating element, the resistive heating element being configured to generate heat in response to electrical power.

Example 18

The apparatus of any one or more of Examples 15 through 17, further comprising an electrical power source, the thermal heating element being configured to generate heat in response to electrical power from the thermal heating element.

Example 19

The apparatus of claim 18, further comprising one or more wires extending along the shaft, the one or more wires coupling the thermal heating element with the electrical power source.

Example 20

The apparatus of any one or more of Examples 15 through 19, the balloon being formed of silicone.

Example 21

The apparatus of any one or more of Examples 15 through 20, the heating element being operable to heat fluid inflating the balloon.

Example 22

The apparatus of claim 21, the heating element and the balloon being operable to apply heat to tissue contacting the balloon at a temperature of at least approximately 45 degrees Celsius.

Example 23

The apparatus of any one or more of Examples 21 through 22, further comprising a circulating element, the circulating element being operable to circulate fluid inflating the balloon to thereby distribute heat within the fluid inflating the balloon.

Example 24

The apparatus of claim 23, the circulating element including a fluid inlet and a fluid outlet.

Example 25

The apparatus of claim 24, the fluid inlet and the fluid outlet being positioned within the balloon.

Example 26

The apparatus of any one or more of Examples 21 through 25, further comprising a temperature sensor, the temperature sensor being operable to sense temperature of fluid within the balloon.

Example 27

The apparatus of any one or more of Examples 1 through 26, further comprising a position sensor, the position sensor being operable to generate signals indicating a position of the balloon in three-dimensional space.

Example 28

The apparatus of claim 27, the position sensor including a coil configured to generate signals in response to alternating electromagnetic fields.

Example 29

The apparatus of any one or more of Examples 1 through 28, further comprising a guide element defining a bent distal region, the guide element being configured to guide the balloon into a Eustachian tube as the shaft is advanced distally relative to the guide element.

Example 30

The apparatus of claim 29, the guide element including a steerable distal end, the steerable distal end being configured to enable an operator to bend the distal region to achieve a selected bend angle.

Example 31

The apparatus of any one or more of Examples 29 through 30, the shaft and the balloon being slidably disposed within the guide element.

Example 32

An apparatus, comprising: (a) a shaft defining a lumen, the shaft having a first outer diameter; (b) a balloon at the distal end of the shaft, the balloon being in fluid communication with the lumen, the balloon being operable to transition between a non-expanded state and an expanded state, the balloon in the non-expanded state being sized to fit in a Eustachian tube of a patient, the balloon in the expanded state being sized to bear against tissue of the Eustachian tube; and (c) a heating feature, the heating feature being operable to ablate tissue of the Eustachian tube contacting the balloon in the expanded state, the heating feature including: (i) an illuminating element, and (ii) a photosensitive coating on the balloon, the illuminating element being operable to illuminate the photosensitive coating on the balloon, the photosensitive coating being configured to ablate tissue in response to light from the illuminating element.

Example 33

The apparatus of claim 32, further comprising a tip member at the distal end of the shaft, the tip member being positioned distal to the balloon, the tip member having a second outer diameter, the second outer diameter being larger than the first outer diameter.

Example 34

The apparatus of any one or more of Examples 32 through 33, the illuminating element being positioned within an interior region of the balloon.

Example 35

The apparatus of any one or more of Examples 32 through 34, the illuminating element including an LED within an interior region of the balloon.

Example 36

The apparatus of any one or more of claim 35, further comprising an electrical power source in communication with the LED, the electrical power source being operable to activate the LED.

Example 37

The apparatus of any one or more of Examples 32 through 36, the illuminating element including an optically transmissive window on the shaft.

Example 38

The apparatus of claim 37, further comprising a light source, the optically transmissive window being operable to emit light from the light source into the interior region of the balloon.

Example 39

The apparatus of claim 38, further comprising a light conveying feature extending along the shaft, the light conveying feature being configured to optically couple the light source with the optically transmissive window.

Example 40

The apparatus of claim 39, the light conveying feature being selected from the group consisting of a light pipe and an optical fiber.

Example 41

The apparatus of any one or more of Examples 32 through 40, the photosensitive coating comprising hemoglobin.

Example 42

An apparatus, comprising: (a) a shaft defining a lumen, the shaft having a first outer diameter; (b) a balloon at the distal end of the shaft, the balloon being in fluid communication with the lumen, the balloon being operable to transition between a non-expanded state and an expanded state, the balloon in the non-expanded state being sized to fit in a Eustachian tube of a patient, the balloon in the expanded state being sized to bear against tissue of the Eustachian tube; and (c) a heating feature, the heating feature being operable to ablate tissue of the Eustachian tube contacting the balloon in the expanded state, the heating feature including a thermal heating element, the thermal heating element being operable to heat fluid inflating the balloon, the balloon being configured to ablate tissue in response to heating of fluid inflating the balloon.

Example 43

The apparatus of claim 42, the thermal heating element being positioned within an interior region of the balloon.

Example 44

The apparatus of any one or more of Examples 42 through 43, the thermal heating element including a resistive heating element, the resistive heating element being configured to generate heat in response to electrical power.

Example 45

The apparatus of any one or more of Examples 42 through 44, further comprising an electrical power source, the thermal heating element being configured to generate heat in response to electrical power from the thermal heating element.

Example 46

The apparatus of claim 45, further comprising one or more wires extending along the shaft, the one or more wires coupling the thermal heating element with the electrical power source.

Example 47

The apparatus of any one or more of Examples 42 through 46, the balloon being formed of silicone.

Example 48

The apparatus of any one or more of Examples 42 through 47, the heating element and the balloon being operable to apply heat to tissue contacting the balloon at a temperature of at least approximately 45 degrees Celsius.

Example 49

The apparatus of any one or more of Examples 42 through 48, further comprising a circulating element, the circulating element being operable to circulate fluid inflating the balloon to thereby distribute heat within the fluid inflating the balloon.

Example 50

The apparatus of claim 49, the circulating element including a fluid inlet and a fluid outlet.

Example 51

The apparatus of claim 50, the fluid inlet and the fluid outlet being positioned within the balloon.

Example 52

The apparatus of any one or more of Examples 42 through 51, further comprising a temperature sensor, the temperature sensor being operable to sense temperature of fluid within the balloon.

Example 53

The apparatus of any one or more of Examples 42 through 52, further comprising a tip member at the distal end of the shaft, the tip member being positioned distal to the balloon, the tip member having a second outer diameter, the second outer diameter being larger than the first outer diameter.

Example 54

A method comprising: (a) inserting a catheter into a head of a patient, the catheter including an inflatable balloon near a distal end of the catheter; (b) advancing the balloon in a Eustachian tube in the head of the patient, the balloon being in a non-expanded state while advancing the balloon; (c) expanding the balloon while the balloon is in the Eustachian tube; and (d) ablating tissue of the Eustachian tube via the balloon.

Example 55

The method of claim 54, inserting the catheter into the head of the patient including inserting the catheter via a nostril of the patient.

Example 56

The method of claim 54, inserting the catheter into the head of the patient including inserting the catheter via a mouth of the patient.

Example 57

The method of any one or more of Examples 54 through 56, the catheter further including an enlarged distal tip positioned distal to the balloon, the method further comprising arresting advancement of the balloon before the enlarged distal tip traverses an isthmus between the Eustachian tube and a middle ear region of the patient.

Example 58

The method of any one or more of Examples 54 through 57, the act of ablating tissue comprising activating a heating feature associated with the catheter.

Example 59

The method of claim 58, the heating feature including an illuminating element, the act of activating the heating feature comprising emitting light from the illuminating element.

Example 60

The method of claim 59, the illuminating element including an electrically powered light source located within an interior region of the balloon, the act of activating the heating feature further comprising providing electrical power to the electrically powered light source.

Example 61

The method of any one or more of Examples 59 through 60, the illuminating element including an optically transmissive window on a shaft of the catheter.

Example 62

The method of claim 61, the act of activating the heating feature further comprising conveying light from a light source along a light conveying feature extending along the shaft, the light conveying feature being optically coupling the light source with the optically transmissive window.

Example 63

The method of any one or more of Examples 59 through 62, the act of activating the heating feature further comprising conveying light from the illuminating element to a light sensitive coating on the balloon, the light sensitive coating providing the ablating of the tissue in response to light from the illuminating element.

Example 64

The method of any one or more of Examples 54 through 63, the heating feature including a thermal heating element, the act of activating the heating feature comprising emitting heat from the thermal heating element.

Example 65

The method of claim 64, the act of expanding the balloon comprising filling the balloon with a fluid, the fluid conveying heat emitted from the thermal heating element to the balloon to thereby heat the balloon, the heated balloon providing the ablating of the tissue in response to heat from the heating element.

Example 66

The method of any one or more of Examples 64 through 65, the act of activating the heating feature comprising providing electrical power from an electrical power source to the thermal heating element.

Example 67

The method of any one or more of Examples 64 through 66, further comprising recirculating fluid within the balloon.

Example 68

The method of claim 67, the act of recirculating fluid within the balloon being performed during the act of emitting heat from the thermal heating element.

Example 69

The method of any one or more of Examples 64 through 68, further comprising sensing temperature of fluid within the balloon.

Example 70

The method of claim 69, further comprising regulating emission of heat from the thermal heating element based on sensed temperature data from the act of sensing temperature.

Example 71

The method of any one or more of Examples 54 through 70, the act of ablating tissue comprising applying heat to tissue contacting the balloon at a temperature of at least approximately 45 degrees Celsius.

Example 72

The method of any one or more of Examples 54 through 71, the act of expanding the balloon comprising expanding the balloon to a point where the balloon contacts tissue of the Eustachian tube along at least a portion of the length of the balloon.

Example 73

The method of any one or more of Examples 54 through 72, the act of expanding the balloon comprising expanding the balloon to a point where the balloon dilates the Eustachian tube.

Example 74

The method of any one or more of Examples 54 through 73, further comprising tracking a position of the balloon in the head of the patient based on signals from a position sensor coupled with the catheter.

Example 75

The method of claim 74, the act of tracking a position of the balloon further comprising generating an alternating electromagnetic field around the head of the patient, the position sensor generating signals in response to the alternating electromagnetic field.

Example 76

An apparatus, comprising: (a) a shaft having a first outer diameter and a distal end; (b) a tip member at the distal end of the shaft, the tip member having a second outer diameter, the second outer diameter being larger than the first outer diameter; and (c) an electrode assembly, the electrode assembly including a plurality of electrodes positioned along the shaft near the distal end, the electrode assembly being positioned proximal to the tip member, the electrodes being spaced apart from each other along a longitudinal axis defined by the shaft, the electrodes being operable to apply RF energy to tissue to thereby ablate the tissue.

Example 77

The apparatus of claim 76, each electrode of the plurality of electrodes having an annular shape.

Example 78

The apparatus of any one or more of Examples 76 through 77, the plurality of electrodes being operable to apply bipolar RF energy to tissue to thereby ablate the tissue.

Example 79

The apparatus of claim 78, the plurality of electrodes including a first electrode set and a second electrode set, the electrodes of the first electrode set being configured to serve as active electrodes during application of RF energy to tissue, the electrodes of the second electrode set being configured to serve as return electrodes during application of RF energy to tissue.

Example 80

The apparatus of claim 79, the plurality of electrodes being arranged in an alternating fashion such that electrodes of the first electrode set are positioned between electrodes of the second electrode set along the longitudinal axis.

Example 81

The apparatus of claim 79, the plurality of electrodes being arranged such that the electrodes of the first electrode set are grouped together along a first longitudinal region of the shaft and the electrodes of the second electrode set are grouped together along a second longitudinal region of the electrode shaft.

Example 82

The apparatus of claim 81, the first longitudinal region being distal to the second longitudinal region.

Example 83

The apparatus of any one or more of Examples 76 through 82, the shaft being flexible.

Example 84

The apparatus of any one or more of Examples 76 through 83, the electrode assembly further comprising a resilient spine.

Example 85

The apparatus of claim 84, the resilient spine including nitinol.

Example 86

The apparatus of any one or more of Examples 76 through 85, further comprising a position sensor, the position sensor being operable to generate signals indicating a position of the balloon in three-dimensional space.

Example 87

The apparatus of claim 86, the position sensor including a coil configured to generate signals in response to alternating electromagnetic fields.

Example 88

The apparatus of any one or more of Examples 1 through 87, further comprising a guide element defining a bent distal region, the guide element being configured to guide the balloon into a Eustachian tube as the shaft is advanced distally relative to the guide element.

Example 89

The apparatus of claim 88, the guide element including a steerable distal end, the steerable distal end being configured to enable an operator to bend the distal region to achieve a selected bend angle.

Example 90

The apparatus of any one or more of Examples 88 through 89, the shaft and the electrode assembly being slidably disposed within the guide element.

Example 91

A method comprising: (a) inserting a catheter into a head of a patient, the catheter including a shaft and an electrode assembly, the electrode assembly including a plurality of electrodes positioned along the shaft near the distal end, the electrodes being spaced apart from each other along a longitudinal axis defined by the shaft: (b) advancing the electrode assembly in a Eustachian tube in the head of the patient; and (c) activating the electrode assembly to thereby ablate tissue of the Eustachian tube via RF ablation.

Example 92

The method of claim 91, inserting the catheter into the head of the patient including inserting the catheter via a nostril of the patient.

Example 93

The method of claim 91, inserting the catheter into the head of the patient including inserting the catheter via a mouth of the patient.

Example 94

The method of any one or more of Examples 91 through 93, the catheter further including an enlarged distal tip positioned distal to the electrode assembly, the method further comprising arresting advancement of the electrode assembly before the enlarged distal tip traverses an isthmus between the Eustachian tube and a middle ear region of the patient.

Example 95

The method of any one or more of Examples 91 through 94, the act of ablating the tissue including applying bipolar RF energy to the tissue via the electrode assembly.

Example 96

The method of any one or more of Examples 91 through 94, the act of ablating the tissue including applying monopolar RF energy to the tissue via the electrode assembly.

Example 97

The method of any one or more of Examples 91 through 96, each electrode of the plurality of electrodes having an annular shape, the act of ablating tissue being performed while an entire surface of at least two of the electrodes is in contact with the tissue about the longitudinal axis.

Example 98

The method of any one or more of Examples 91 through 97, further comprising sensing one or more tissue properties during the act of ablating tissue.

Example 99

The method of claim 98, the one or more tissue properties including one or more of tissue temperature or tissue impedance.

Example 100

The method of any one or more of Examples 91 through 99, further comprising tracking a position of the electrode assembly in the head of the patient based on signals from a position sensor coupled with the catheter.

V. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a fluid connector;
   (b) a shaft defining a lumen, the shaft having a first outer diameter, a proximal end, and a distal end, the proximal end being coupled with the fluid connector;
   (c) a balloon at the distal end of the shaft, the balloon being in fluid communication with the lumen, the balloon being operable to transition between a non-expanded state and an expanded state, the balloon in the non-expanded state being sized to fit in a Eustachian tube of a patient, the balloon in the expanded state being sized to bear against tissue of the Eustachian tube, the shaft being flexible from the fluid connector to a proximal portion of the balloon;
   (d) a tip member at the distal end of the shaft, the tip member being positioned distal to the balloon, the tip member having a second outer diameter, the second outer diameter being larger than the first outer diameter; and
   (e) a heating feature being positioned axially along the longitudinal axis of the shaft and having the first outer diameter such that there is a constant diameter from the shaft to the heating feature so as to allow the balloon to wrap around the shaft and the heating feature to thereby include a first outer diameter inner portion, the heating feature being operable to ablate tissue of the Eustachian tube contacting the balloon in the expanded state, the heating feature including a thermal heating element, the thermal heating element being operable to heat fluid inflating the balloon, the balloon being configured to ablate tissue in response to heating of fluid inflating the balloon.

2. The apparatus of claim 1, the balloon being formed of a non-extensible material.

3. The apparatus of claim 1, the tip member having a bulb shape.

4. The apparatus of claim 1, the second outer diameter being sized to prevent the tip member from passing through an isthmus between a Eustachian tube and middle ear of a patient.

5. The apparatus of claim 1, the heating feature including a thermal heating element.

6. The apparatus of claim 5, the thermal heating element being positioned within an interior region of the balloon.

7. The apparatus of claim 5, the balloon being formed of silicone.

8. The apparatus of claim 5, the heating element being operable to heat fluid inflating the balloon.

9. The apparatus of claim 8, the heating element and the balloon being operable to apply heat to tissue contacting the balloon at a temperature of at least approximately 45 degrees Celsius.

10. The apparatus of claim 8, further comprising a temperature sensor, the temperature sensor being operable to sense temperature of fluid within the balloon.

11. The apparatus of claim 1, the apparatus further including a circulating pump positioned within the shaft and configured to recirculate fluid within the balloon.

12. The apparatus of claim 11, the shaft being flexible from the fluid connector to beyond a distal end of the balloon in a distal direction.

13. The apparatus of claim 1, further comprising a guide element defining a bent distal region, the guide element being configured to guide the balloon into a Eustachian tube as the shaft is advanced distally relative to the guide element.

14. An apparatus, comprising:
   (a) a shaft defining a lumen and a longitudinal axis, the shaft having a first outer diameter and a distal end;
   (b) a balloon at the distal end of the shaft, the balloon being in fluid communication with the lumen, the balloon being operable to transition between a non-expanded state and an expanded state, the balloon in the non-expanded state being sized to fit in a Eustachian tube of a patient, the balloon in the expanded state being sized to bear against tissue of the Eustachian tube; and
   (c) a heating feature being positioned axially along the longitudinal axis of the shaft and having the first outer diameter such that there is a constant diameter from the shaft to the heating feature so as to allow the balloon to wrap around the shaft and the heating feature to thereby include a first outer diameter inner portion, the heating feature being operable to ablate tissue of the Eustachian tube contacting the balloon in the expanded state, the heating feature including a thermal heating element, the thermal heating element being operable to heat fluid inflating the balloon, the balloon being configured to ablate tissue in response to heating of fluid inflating the balloon,
   the balloon having an inner surface facing the shaft and the heating feature,
   the shaft and the heating feature each having the first outer diameter along a length of the balloon to thereby allow the inner surface of the balloon to assume the first outer diameter along the length of the balloon while the balloon is in the non-expanded state.

15. The apparatus of claim 14, further comprising a power source operable to power the heating feature, the power source and the heating feature being in electrical communication via an electrical conduit extending through at least a portion of the shaft.

* * * * *